United States Patent
Riley et al.

(10) Patent No.: US 9,421,009 B1
(45) Date of Patent: Aug. 23, 2016

(54) SUTURE DELIVERY SYSTEM

(71) Applicants: A. Jamie Riley, St. Louis, MO (US);
Gary J. Schmidt, St. Louis, MO (US);
Amod P. Paranjpe, Augusta, MO (US)

(72) Inventors: A. Jamie Riley, St. Louis, MO (US);
Gary J. Schmidt, St. Louis, MO (US);
Amod P. Paranjpe, Augusta, MO (US)

( * ) Notice: Subject to any disclaimer, the term of this patent is extended or adjusted under 35 U.S.C. 154(b) by 0 days.

(21) Appl. No.: 13/629,263

(22) Filed: Sep. 27, 2012

Related U.S. Application Data

(60) Provisional application No. 61/539,774, filed on Sep. 27, 2011.

(51) Int. Cl.
*A61B 17/04* (2006.01)

(52) U.S. Cl.
CPC .................................. *A61B 17/0401* (2013.01)

(58) Field of Classification Search
CPC ............... A61B 17/0401; A61B 17/04; A61B 17/0483; A61B 17/0482; A61B 17/0485; A61B 17/06114; A61B 17/06123; A61B 17/06128; A61B 17/06133; A61B 17/06138; A61B 17/06119; A61B 2017/0414; A61B 2017/0479; A61B 2017/06142
See application file for complete search history.

(56) References Cited

U.S. PATENT DOCUMENTS

| | | | |
|---|---|---|---|
| 4,699,271 A * | 10/1987 | Lincoln | G06F 8/313 206/380 |
| 5,478,344 A | 12/1995 | Stone et al. | |
| 5,478,345 A | 12/1995 | Stone et al. | |
| 5,486,186 A | 1/1996 | Yoon | |
| 5,591,181 A | 1/1997 | Stone et al. | |
| 5,628,395 A * | 5/1997 | Daniele | A61B 17/06133 206/227 |
| 5,630,825 A | 5/1997 | de la Torre et al. | |
| 6,016,905 A * | 1/2000 | Gemma | A61B 17/06133 206/380 |
| 6,126,666 A | 10/2000 | Trapp et al. | |
| 6,481,568 B1 * | 11/2002 | Cerwin | A61B 17/06133 206/339 |
| 7,615,061 B2 | 11/2009 | White et al. | |
| 7,963,972 B2 | 6/2011 | Foerster et al. | |
| 2007/0010832 A1 | 1/2007 | Manzo | |
| 2008/0033460 A1 | 2/2008 | Ziniti et al. | |
| 2010/0116694 A1 * | 5/2010 | Stopek | A61B 17/06133 206/210 |
| 2011/0046642 A1 | 2/2011 | McClurg et al. | |
| 2011/0215005 A1 * | 9/2011 | Cerwin | A61B 17/06133 206/63.3 |

OTHER PUBLICATIONS

International Search Report and Written Opinion dated Feb. 15, 2013 from corresponding PCT Application.

* cited by examiner

*Primary Examiner* — Jocelin Tanner
(74) *Attorney, Agent, or Firm* — Armstrong Teasdale LLP

(57) ABSTRACT

A suture delivery system includes a distal portion having a central opening therein and one or more flanges surrounding said central opening; a body portion connected with said distal portion; and at least one suture strand and needle combination removably connected with at least one of said distal portion and said body portion, wherein a first portion of said suture strand engages said flanges of said distal portion and said body portion stores a second portion of said suture strand and said needle.

28 Claims, 5 Drawing Sheets

SUTURE DELIVERY SYSTEM

CROSS REFERENCES

This application claims priority to U.S. Provisional Patent Application No. 61/539,774, filed Sep. 27, 2011.

TECHNICAL FIELD OF THE INVENTION

The present invention relates generally to surgical tools and, more particularly, to a device for enhancing the process of reconnecting soft tissue with underlying bone structures.

BACKGROUND OF THE INVENTION

Staples and orthopedic washers have been used for many years to surgical attach soft tissues to underlying bone structures. Prior art staples are metallic "U"-shaped structures wherein the legs of the staple are driven into the underlying bone structure to sandwich the soft tissue between a web that connects the legs of the staple and the underlying bone. Examples of such staples are described in U.S. Pat. Nos. 4,592,346 and 4,793,335.

Prior art orthopedic washers are typically round or oval in shape with an open center and provided with multiple sharp pins as well as blunt posts on the underside of the washer. The washer is secured to the bone by a screw. Similarly to the prior art staples described above, the soft tissue that is to be secured is sandwiched between the washer and the underlying bone. The washer is held in place by the screw and sharp pins, while the blunt posts ensure that sufficient space is maintained between the washer and the bone to avoid damaging the soft tissue being secured.

In each case, these prior art devices are intended to ensure proper contact between the bone and soft tissue, with some degree of compression being exerted, to facilitate reconnection of the soft tissue to the bone. In the case of each type of device, the device is also used as an anchor for sutures that are used to further secure a larger area of soft tissue. These devices are used, for example, to reinforce fracture sites, to reduce potential space between the bone and overlying soft tissue, and to promote vascularity to the periosteal surface.

However, these prior art devices suffer from several drawbacks. First, the nature of these devices requires that they be constructed of a metallic or hard plastic material. Further, the device remains in the body following the subject procedure. Thus, the use of these prior art devices involves the introduction and continued presence—coupled with the possible need for subsequent removal—of an additional foreign body in the patient. This creates a possible additional avenue for infection at the surgical site. Further, it subjects these devices to significant regulation, which in turn increases the cost of producing the devices.

Therefore, it would be advantageous to provide a device that facilitates anchoring of sutures for securing soft tissue to underlying bone structures yet is removable prior to suturing.

SUMMARY OF THE INVENTION

One aspect of the invention generally pertains to a suture delivery system that provides quick and accurate placement and secure and repeatable anchoring of one or more sutures at a fixation site.

Another aspect of the invention generally pertains to a suture delivery system that is removable prior to suturing and capable of using low cost, disposable materials in its construction.

In accordance with the above aspects of the invention, there is provided a suture delivery system that includes a distal portion having a central opening; a body portion; and at least one suture strand and needle combination removably connected with at least one of the distal, or body portions.

These aspects are merely illustrative of the innumerable aspects associated with the present invention and should not be deemed as limiting in any manner. These and other aspects, features and advantages of the present invention will become apparent from the following detailed description when taken in conjunction with the referenced drawings.

BRIEF DESCRIPTION OF THE DRAWINGS

Reference is now made more particularly to the drawings, which illustrate the best presently known mode of carrying out the invention and wherein similar reference characters indicate the same parts throughout the views.

DETAILED DESCRIPTION

In the following detailed description numerous specific details are set forth in order to provide a thorough understanding of the invention. However, it will be understood by those skilled in the art that the present invention may be practiced without these specific details. For example, the invention is not limited in scope to the particular type of industry application depicted in the figures. In other instances, well-known methods, procedures, and components have not been described in detail so as not to obscure the present invention.

Figure 1:
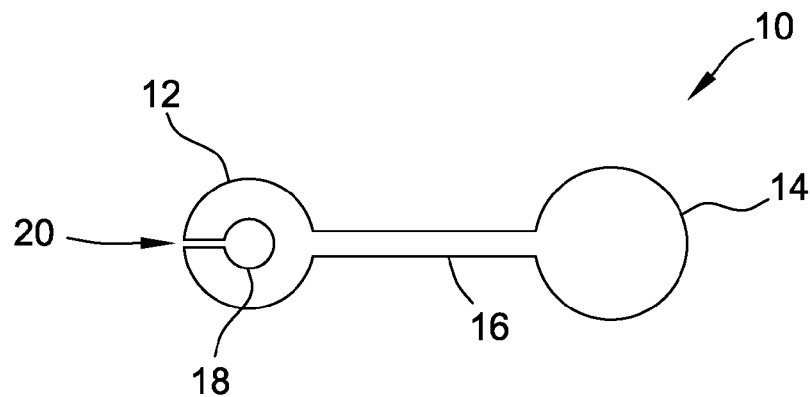
FIG. 1 is a top view of a suture delivery system according to an embodiment of the present invention.
Figure 2:
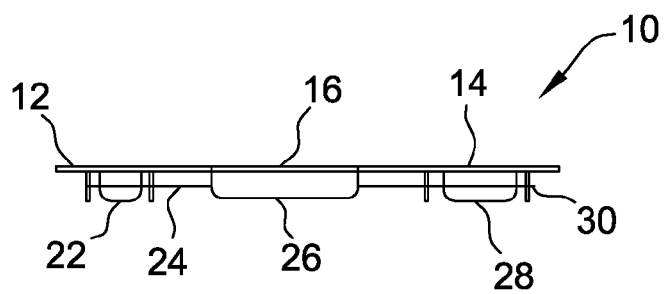
FIG. 2 is a side view of the suture delivery system of FIG. 1.
Figure 3:
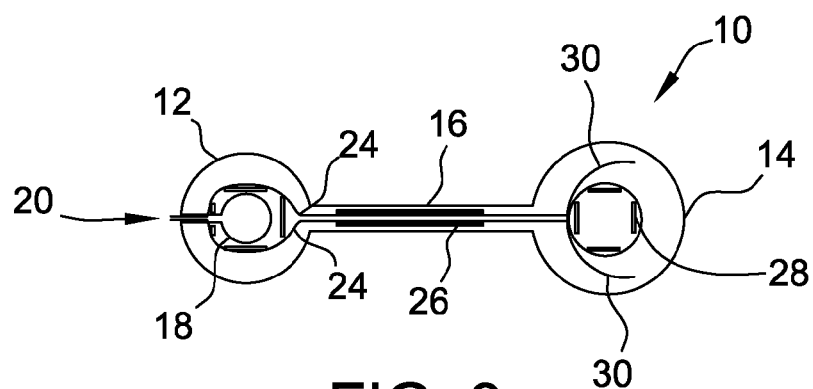
FIG. 3 is a bottom view of the suture delivery system of FIG. 1.

FIGS. 1-3 illustrate a suture delivery system according to an embodiment of the present invention. The system includes a base 10. In the illustrated embodiment, the base 10 is provided with a roughly hourglass shape composed of a distal 12 portion and a body portion that is formed by a proximal 14 portion and an extended handle portion 16. Distal portion 12, alternately referenced as a suture loop snare, is advantageously provided with a central opening 18, which accommodates a surgical screw as described in more detail below. Distal portion 12 is also be provided with a break or slot 20 in one side, preferably the side opposite of the connection between the distal portion 12 and the handle 16, to facilitate removal of the base 10 from the surgical screw after implantation of the screw in the underlying bone. Thus, the distal portion 12 will have what may be considered to be "C" shape.

The underside, or middle, of the distal portion 12 is provided with one or more slots or flanges 22 to capture a portion of several suture strands 24 that are advantageously packaged with the base 10 to form the system. The flanges 22 of the distal portion 12 route the suture strands 24 around the central opening 18 of the distal portion so that they do not interfere with the initial insertion of a surgical screw through the central opening 18. However, the flanges 22 do position the suture strands immediately adjacent to the edges of the central opening 18 to encourage capture of the suture strands by the surgical screw. This arrangement results in a portion of the suture strands being wrapped around the surgical screw to form an extremely solid base connection for the suture strands 24. It should be noted that the suture strands 24 are preferably arranged such that the middle section of each suture strand 24 is positioned in the flanges 22 of the distal portion 12.

The underside of the handle 16 portion of the base 10 is also provided with slots or flanges 26 to capture the bulk of the suture strands 24 packaged with the system. Alternately, the handle portion 16 may be composed of a pair of horizontal surfaces with the suture strands sandwiched therebetween. In yet another embodiment, the handle portion 16 is formed into a tube through which the suture strands 24 are threaded in preparation for delivery. In essence, the underside of the handle 16 serves as the primary storage area for the suture strands 24. The flanges 26 of the handle open toward the bottom to allow the suture strands to be released from the handle after placement of the base 10 and implantation of the surgical screw.

In a similar manner, the underside of the proximal portion 14 is provided with slots or flanges 28 to capture needles 30 that are pre-threaded onto the suture strands 24. Thus, after implantation of the surgical screw, and the resultant fixation of the suture strands 24 at the implantation site, needles are immediately available to the surgeon to begin suturing.

As alluded to above, the base 10 serves primarily as an advantageous initial delivery system to ensure quick and accurate placement and, significantly, secure and repeatable anchoring of the suture strands 24 by the surgical screw. Once the surgical screw has been inserted through the central opening 18 of the distal portion 12 and then secured into the underlying bone, which, again, involves capture of the middle portion of the suture strands 24 to anchor those strands, the base 10 is removed by simply passing the surgical screw through the slot 20 of the distal portion 12 and pulling the base 10 away from the suture strands 24 and needles 30. This leaves the site completely unobstructed with the suture strands 24 and needles 30 perfectly positioned for subsequent suturing. Furthermore, the suture strands 24 are securely anchored by the surgical screw.

An additional advantage of the described system is that the base 10 can be constructed of low cost, flexible plastic material or reinforced paper. The base 10 is intended to be a single use, disposable unit.

While the illustrated embodiment has been described in connection with the use of a surgical screw, the system may be utilized with essentially any known surgical hardware, including staples or rivets, in the same manner as described above.

A further advantage of the described system is that the base 10 may also be used for the application of bone wax to the fixation point. Bone wax may be applied to the underside of the distal portion 12 surrounding the central opening 18 during manufacture of system and prior to packaging.

Figure 4:
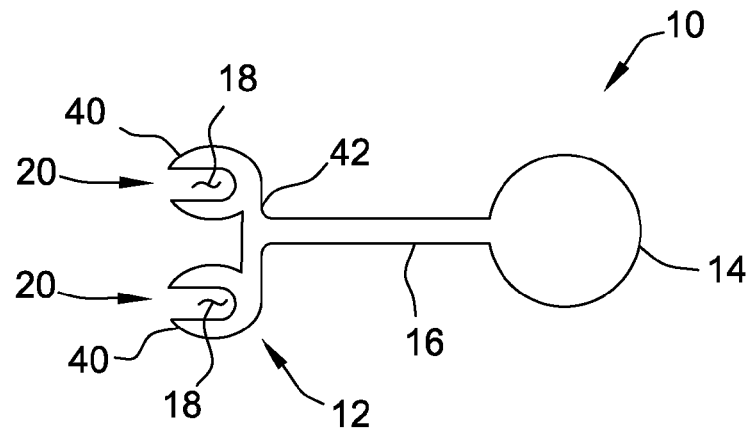
FIG. 4 is a top view of a suture delivery system according to another embodiment.
Figure 5:
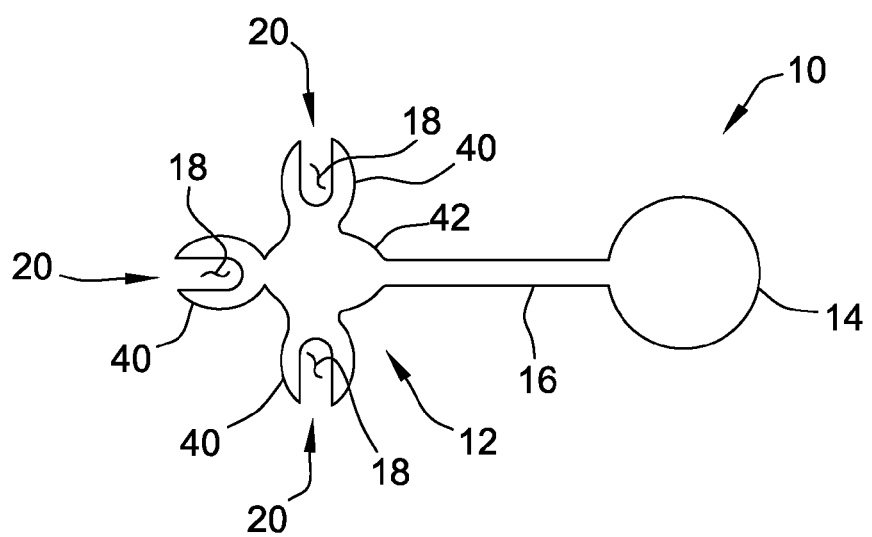
FIG. 5 is a top view of a suture delivery system according to yet another embodiment.

FIGS. 4 and 5 illustrate additional embodiments of a suture delivery system. The primary difference between the versions in these figures and the embodiments described above resides in the use of multiple suture snares in the distal portion 12 of these embodiments. More particularly, FIG. 4 illustrates a version utilizing two snares 40. As with the previously described embodiment, each snare 40 is generally C-shaped with a break or slot 20 in one side, preferably the side opposite of the connection between the snare 40 and a connecting portion 42 that connects the snares 40 with the handle portion 16, to facilitate removal of the base 10 from the surgical screw after implantation of the screw in the underlying bone. The underside, or middle, of each snare 40 is provided with one or more slots or flanges 22 to capture a portion of the suture strands 24. This embodiment is particularly useful for forming a suture bridge that is anchored to the surgical screw.

FIG. 5 illustrates a version utilizing three snares 40. As with the previously described embodiment, each snare 40 is generally C-shaped with a break or slot 20 in one side, preferably the side opposite of the connection between the snare 40 and a connecting portion 42 that connects the snares 40 with the handle portion 16, to facilitate removal of the base 10 from the surgical screw after implantation of the screw in the underlying bone. The underside, or middle, of each snare 40 is provided with one or more slots or flanges 22 to capture a portion of the suture strands 24. The embodiment of FIG. 5 is particularly useful for forming an enhanced tangential anchor site or for enhanced radial pull of soft tissue to the anchor site(s).

The remaining portions of the embodiments of FIGS. 4 and 5 are essentially the same as the previously described embodiments.

Figure 6:
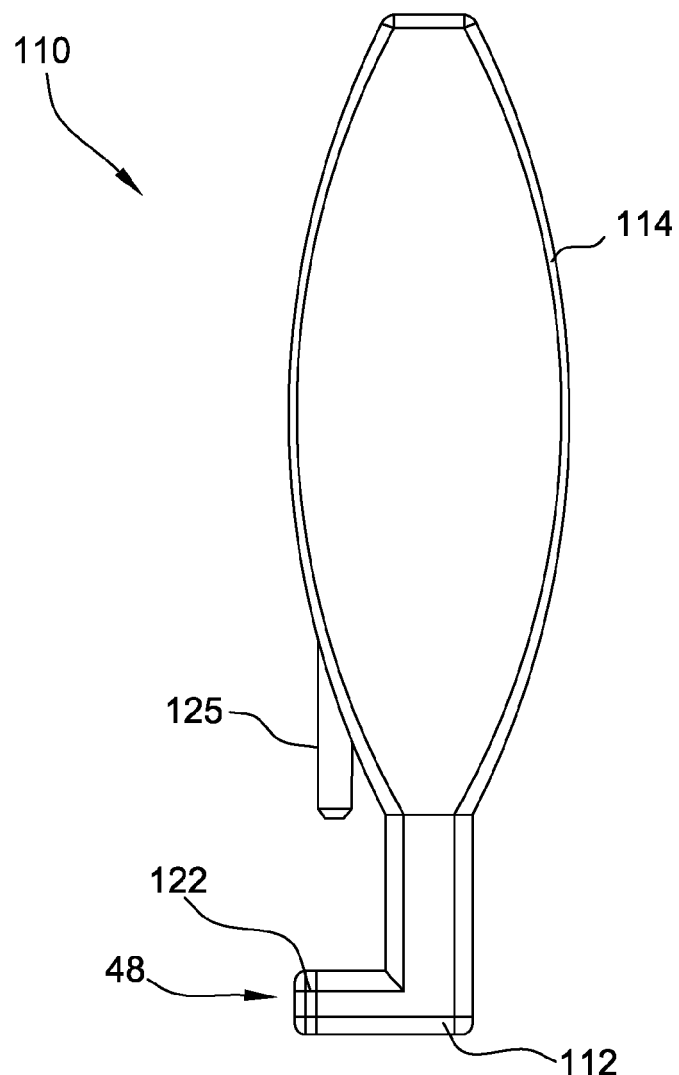
FIG. 6 is a side view of another embodiment of a suture delivery system.
Figure 7:
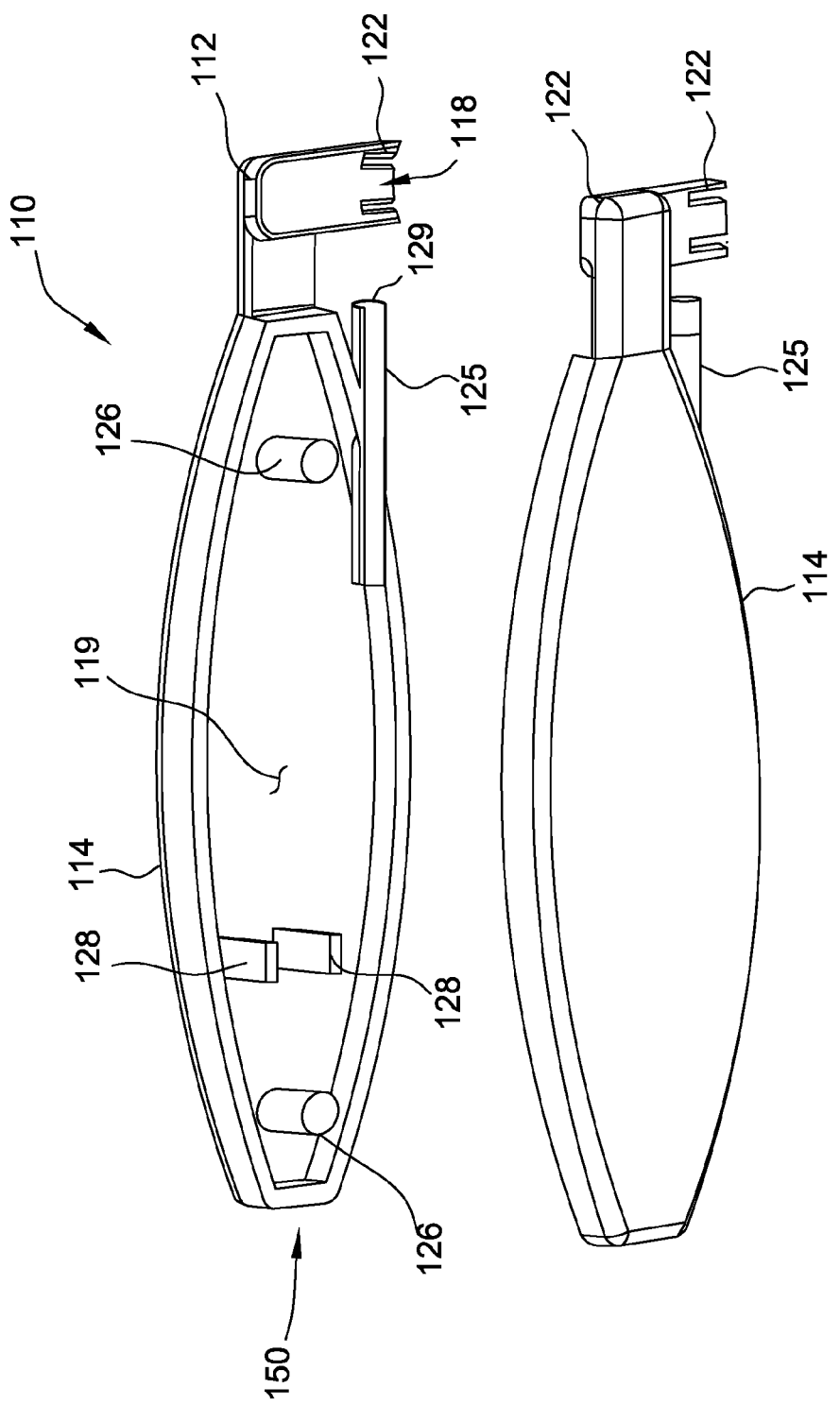
FIG. 7 is a perspective view of the embodiment of FIG. 6 in which the two halves of the device are separated from one another.
Figure 8:
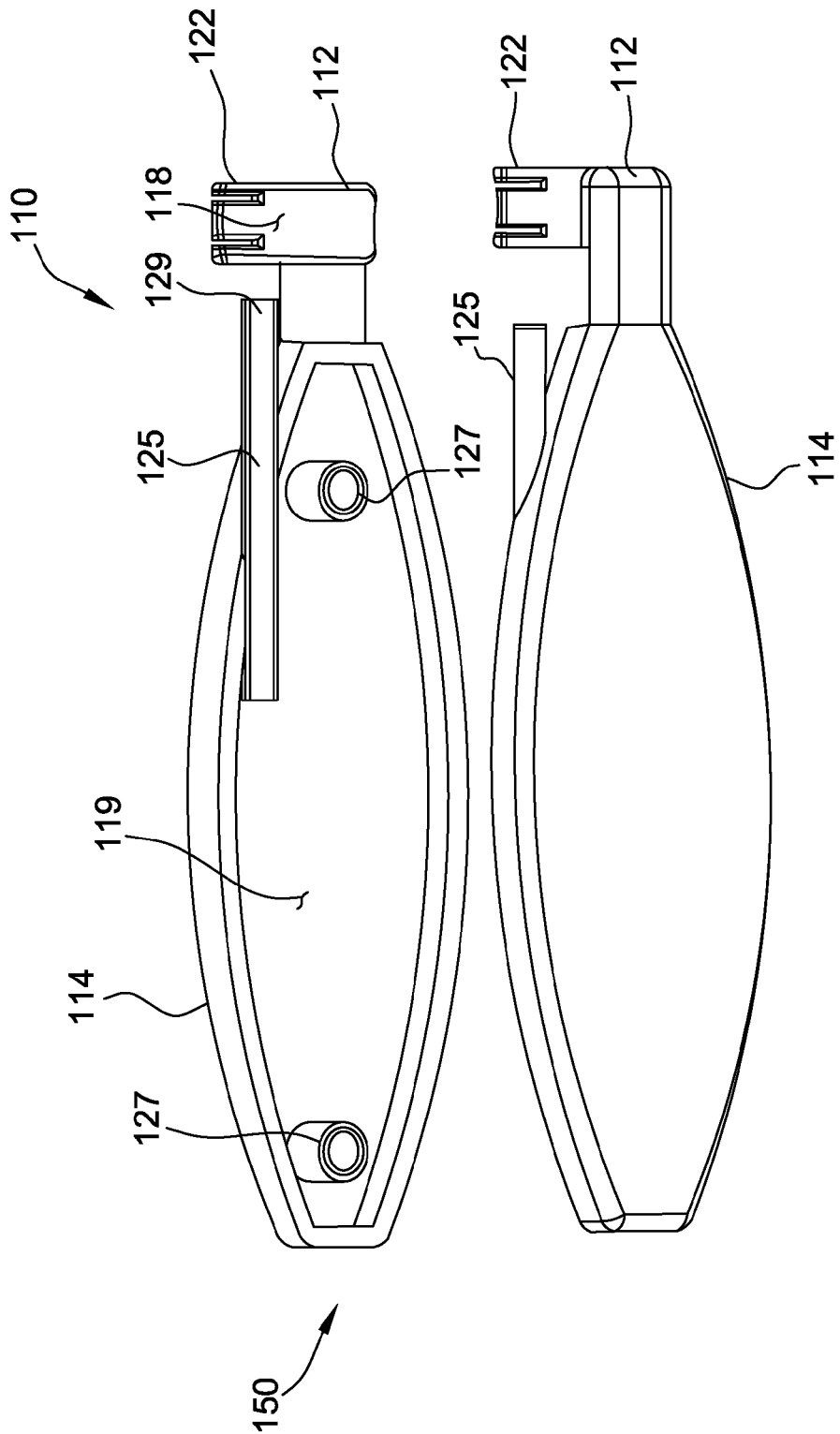
FIG. 8 is a perspective view of the two halves of the device of FIGS. 6 and 7 from the opposite direction of FIG. 7.

FIGS. 6-8 illustrate another embodiment utilizing a slightly different shape. In this embodiment, the base 110 also has a distal portion 112 and a body portion 114. Advantageously, the base 110, which may be molded from a plastic or other suitable material, is composed of two, separable halves, creating a "clam-shell" type package. FIGS. 7 and 8 show the two halves of the base 110 separated from one another so that the interior of the base 110 can be seen. As discussed in more detail below, the two halves of the base 110 are separated from one another after the surgical screw has been inserted through the distal portion 112 and implanted in order to access the suture material and remove the base 110 from the surgical site.

The distal portion 112 is generally cylindrically shaped with an open vertical interior space with openings at its top and bottom. This arrangement allows a surgical screw to be inserted through the central opening 118 of the distal portion 112 for implantation. The top end of the distal portion 112 is provided with a series of slots 122. These slots 122 perform the same function as the slots/flanges 22 in the above described embodiments. In particular, they serve to capture a portion of several suture strands that are packaged with the base 110. The slots 122 route the suture strands around the central opening 118 of the distal portion 112 so that they do not interfere with the initial insertion of the surgical screw but are positioned immediately adjacent to the central opening 118 to encourage the screw to capture the suture strands. Again, this results in a portion of the suture strands being wrapped around the surgical screw to form an extremely solid base connection for the suture strands.

The interior of the body portion 114 of the base 110 provides a suitable interior space 119 to house the bulk of the suture strands for the system. The interior 119 of the body portion 114 is provided with a pair of posts 126 in one half of the body portion 114 and a corresponding pair of mating bosses 127 in the other half of the body portion. When the two halves of the base 110 are pressed together, the posts 126 fit into the bosses 127 in a press fit or snap fit manner to secure the two halves together. Advantageously, the posts 126 and bosses 127 provide a structure around which the suture strands may be wrapped to minimize tangling of the suture strand within the body portion 114.

The body portion 114 is also provided with a port 150 that allows the interior of the body portion to be filled with a fluid material. This is advantageous as surgeons frequently soak sutures in various materials, for example, antibiotics or bone growth stimulants, prior to use. The open interior space of the body portion 114 with the port provides a means to pre-soak the suture. In a preferred embodiment, the port is provided with a resealable closure. The resealable closure may simply be a rubber seal through which a syringe needle may be inserted. In an alternate embodiment, a proprietary needle lock is incorporated into the port to allow for a measure of control over what substances may be injected into the body portion 114

The body portion 114 is also provided with a leader tube 125 that communicates with the interior of the body portion 114 and extends horizontally from the body portion 114 toward the top end of the distal portion 112. The leader tube 125 is provided with a distal orifice 129 at its distal end. During assembly of the system, the suture strands are routed from the interior of the body portion 114, through the leader tube 125, and to the slots 122 of the distal portion 112.

The interior 119 of the body portion 114 is also provided with one or more flanges 128 that capture needles that are pre-threaded onto the suture strands. Again, this provides immediately available needles to the surgeon and results in a complete suture package.

This embodiment operates in the same basic manner as the embodiments described above. The base 110 serves primarily as an advantageous initial delivery system to ensure quick and accurate placement and, significantly, secure and repeatable anchoring of the suture strands by the surgical screw. Once the surgical screw has been inserted through the central opening 118 of the distal portion 112 and then secured into the underlying bone, which, again, involves capture of the middle portion of the suture strands to anchor those strands, the base 110 is removed by separating the two halves of the base 110 and pulling the base 110 away from the suture strands and needles. This leaves the site completely unobstructed with the suture strands and needles perfectly positioned for subsequent suturing. Furthermore, the suture strands are securely anchored by the surgical screw.

An additional advantage of the described system is that the base 10 can be constructed of low cost, flexible plastic material or reinforced paper. The base 10 is intended to be a single use, disposable unit.

The preferred embodiments of the invention have been described above to explain the principles of the invention and its practical application to thereby enable others skilled in the art to utilize the invention in the best mode known to the inventors. However, as various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by the above-described exemplary embodiment, but should be defined only in accordance with the following claims appended hereto and their equivalents.

What is claimed is:

1. A suture delivery system comprising:
    a distal portion having a central opening therein and one or more flanges surrounding said central opening, wherein the central opening is configured to receive a screw inserted therethrough;
    a body portion connected with said distal portion and defining an interior cavity, wherein said distal portion and said body portion are divided and comprise two separable parts, wherein said body portion further comprises an elongated tube having first and second orifices at each end thereof, said first orifice of said elongated tube communicating with said interior cavity of said body portion and said second orifice of said elongated tube extending toward one or more flanges of said distal portion; and
    at least one suture strand and needle combination removably connected with at least one of said distal portion and said body portion, wherein a first portion of said suture strand engages one or more flanges of said distal portion and said body portion stores a second portion of said suture strand and said needle.

2. The suture delivery system as set forth in claim 1, wherein said distal portion further comprises a generally cylindrical shape with said central opening passing through said cylindrical shape and said one or more flanges being adjacent a top end of said cylindrical shape.

3. The suture delivery system as set forth in claim 1, wherein said two separable parts form an interior of said body portion, said interior further comprising at least a first inwardly extending structure operable to retain said second portion of said suture strand and at least a second inwardly extending structure operable to retain said needle.

4. The suture delivery system as set forth in claim 1, wherein said two separable parts form an interior of said body portion, said body portion further defining a port therein operable to allow said interior to be filled with a fluid material.

5. The suture delivery system as set forth in claim 4, wherein said port is resealable.

6. The suture delivery system as set forth in claim 1, wherein said body portion further comprises a proximal portion and a handle, said handle connecting said proximal portion with said distal portion.

7. The suture delivery system as set forth in claim 1, wherein said distal and body portions are made of reinforced paper material.

8. The suture delivery system as set forth in claim 1, wherein said distal and body portions are molded.

9. The suture delivery system as set forth in claim 1, wherein said distal and body portions are formed by first and second clam-shell sections.

10. A suture delivery system comprising:
    a base comprising:
        a distal portion defining a central opening therethrough and comprising at least one slot oriented about the central opening, wherein the central opening is configured to receive a threaded member therethrough, and wherein said at least one slot is configured to route a first portion of a suture strand about the central opening such that the threaded member engages the first suture portion when inserted; and
        a body portion extending from said distal portion, wherein said base comprises two separable halves, wherein each half comprises a portion of said distal portion and a portion of said body portion, wherein said body portion defines an interior cavity configured to house a second portion of the suture strand and at least one needle such that the suture strand extends between said body portion and said distal portion, said body portion further comprises an elongated tube having first and second orifices at each end thereof, said first orifice of said elongated tube communicating with said interior cavity of said body portion and said second orifice of said elongated tube extending toward said at least one slot of said distal portion.

11. The suture delivery system in accordance with claim 10, wherein said two separable halves includes a first half including at least one boss and a second half including at least one post configured to engaged said at least one boss to facilitate removably coupling said first half to said second half.

12. The suture delivery system in accordance with claim 11, wherein said at least one boss and said at least one post are configured to support the second portion of the suture strand.

13. The suture delivery system in accordance with claim 10, wherein said distal portion defines a substantially cylindrical shape, and wherein said at least one slot is formed at an end of the cylindrical shape.

14. The suture delivery system in accordance with claim 10, wherein said body portion comprises at least one flange extending toward the interior cavity, said at least one flange configured to support at least one needle.

15. The suture delivery system in accordance with claim 10, wherein said elongated tube is configured to guide the suture strand from the interior cavity to said at least one slot.

16. A suture delivery system comprising:
a distal portion comprising a generally cylindrical shape with a central opening passing through said cylindrical shape and one or more flanges surrounding said central opening, said one or more flanges being adjacent a top end of said distal portion, wherein the central opening is configured to receive a screw inserted therethrough;
a body portion connected with said distal portion and defining an interior cavity, wherein said body portion further comprises an elongated tube having first and second orifices at each end thereof, said first orifice of said elongated tube communicating with said interior cavity of said body portion and said second orifice of said elongated tube extending toward one or more flanges of said distal portion; and
at least one suture strand and needle combination removably connected with at least one of said distal portion and said body portion, wherein a first portion of said suture strand engages one or more flanges of said distal portion and said body portion stores a second portion of said suture strand and said needle.

17. The suture delivery system as set forth in claim 16, wherein said distal portion and said body portion are divided and comprise two separable parts.

18. The suture delivery system as set forth in claim 17, wherein said two separable parts form an interior of said body portion, said interior further comprising at least a first inwardly extending structure operable to retain said second portion of said suture strand and at least a second inwardly extending structure operable to retain said needle.

19. The suture delivery system as set forth in claim 17, wherein said two separable parts form an interior of said body portion, said body portion further defining a port therein operable to allow said interior to be filled with a fluid material.

20. The suture delivery system as set forth in claim 19, wherein said port is resealable.

21. The suture delivery system as set forth in claim 16, wherein said distal and body portions are molded.

22. The suture delivery system as set forth in claim 16, wherein said distal and body portions are formed by first and second clam-shell sections.

23. A suture delivery system comprising:
a base comprising:
a distal portion defining a generally cylindrical shape with a central opening passing through said cylindrical shape, said distal portion comprising one or more flanges surrounding said central opening adjacent a top end of said distal portion, wherein said one or more flanges are configured to form at least one slot oriented about the central opening, wherein the central opening is configured to receive a threaded member therethrough, and wherein said at least one slot is configured to route a first portion of a suture strand about the central opening such that the threaded member engages the first suture portion when inserted; and
a body portion extending from said distal portion, wherein said body portion defines an interior cavity configured to house a second portion of the suture strand and at least one needle such that the suture strand extends between said body portion and said distal portion, said body portion further comprises an elongated tube having first and second orifices at each end thereof, said first orifice of said elongated tube communicating with said interior cavity of said body portion and said second orifice of said elongated tube extending toward one or more flanges of said distal portion.

24. The suture delivery system as set forth in claim 23, wherein said base comprises two separable halves, wherein each half comprises a portion of said distal portion and a portion of said body portion.

25. The suture delivery system in accordance with claim 24, wherein said two separable halves includes a first half including at least one boss and a second half including at least one post configured to engaged said at least one boss to facilitate removably coupling said first half to said second half.

26. The suture delivery system in accordance with claim 25, wherein said at least one boss and said at least one post are configured to support the second portion of the suture strand.

27. The suture delivery system in accordance with claim 23, wherein said body portion comprises at least one flange extending toward the interior cavity, said at least one flange configured to support at least one needle.

28. The suture delivery system in accordance with claim 23, wherein said elongated tube is configured to guide the suture strand from the interior cavity to said at least one slot.

* * * * *